US00PP34791P3

(12) United States Plant Patent
Takahashi

(10) Patent No.: US PP34,791 P3
(45) Date of Patent: Dec. 6, 2022

(54) NECTARINE TREE NAMED 'SWEET REI'

(50) Latin Name: *Prunus persica (L.) Batsch var. nucipersica (Suckow) C.K. Schneid.*
Varietal Denomination: 'SWEET REI'

(71) Applicant: Chukichi Takahashi, Date (JP)

(72) Inventor: Chukichi Takahashi, Date (JP)

( * ) Notice: Subject to any disclaimer, the term of this patent is extended or adjusted under 35 U.S.C. 154(b) by 294 days.

(21) Appl. No.: 16/501,998

(22) Filed: Jul. 18, 2019

(65) Prior Publication Data

US 2020/0029482 P1 Jan. 23, 2020

(30) Foreign Application Priority Data

Jul. 23, 2018 (JP) ..... PBR 33273

(51) Int. Cl.
*A01H 5/08* (2018.01)
*A01H 6/74* (2018.01)

(52) U.S. Cl.
USPC ..... Plt./189
CPC ..... *A01H 6/7454* (2018.05)

(58) Field of Classification Search
USPC ..... Plt./189, 188
CPC ..... A01H 5/0856
See application file for complete search history.

*Primary Examiner* — Kent L Bell
(74) *Attorney, Agent, or Firm* — Oblon, McClelland, Maier & Neustadt, L.L.P.

(57) ABSTRACT

A new and distinct variety of white nectarine tree (*Prunus persica* (L.) Batsch var. *nucipersica* (Suckow) C.K. Schneid.) denominated 'SWEET REI', characterized by being late-maturing, having high Brix and relatively low acidity white flesh, excellent eating quality fruit, being easy to eat because of its freestone fruit, having an attractive dark-red fruit skin color, and no deterioration of eating quality of fruit even after storage for two weeks in a refrigerator.

21 Drawing Sheets

Botanical classification: *Prunus persica* (L.) Batsch var. *nucipersica* (Suckow) C.K. Schneid.
Variety denomination: 'SWEET REI'.

CROSS-REFERENCE TO RELATED APPLICATION

This application claims priority to Japanese Plant Variety Registration Application No. 33273 filed on Jul. 23, 2018, which is incorporated by reference herein as if set forth in its entirety.

BACKGROUND OF THE VARIETY

The present invention relates to a new and distinct variety of white nectarine tree (*Prunus persica* (L.) Batsch var. nucipersica (Suckow) C.K. Schneid.), which has been given the variety denomination 'SWEET REI'. This novel variety was found by natural hybridization of the seed parent variety 'SWEET VENUS' (Japanese Plant Variety Registration No. 12301, registered on Nov. 8, 2004), in Tsukidate-cho, Date-city, Fukushima-prefecture, Japan.

This new white nectarine produces fruits, which are late-maturing, having high brix and relatively low acidity white flesh as well as attractive dark-red skin color, excellent eating quality, and are easy to eat because of its freestone flesh.

ORIGIN OF THE VARIETY

As stated above, the new variety of white nectarine 'SWEET REI' was obtained from natural hybridization of 'SWEET VENUS' (Japanese Plant Variety Registration No. 12301, registered on Nov. 8, 2004), the seed parent of the present variety, in Tsukidate-cho, Date-city, Fukushima-prefecture, Japan, where it was tested.

In 2011, 'SWEET VENUS' was open-pollinated in the inventor's orchard in Tsukidate-cho, Date-city, Fukushima-prefecture, Japan, and 10 of its natural hybrid seeds were seeded and the resultant seedlings were grown at the orchard.

Five (5) germinated seedlings of the above-obtained seedlings were further grown, and the first fruits were observed in 2013. Among the 5 trees from the germinated seedlings, the inventor selected one tree as a mother tree because of its characteristics as having high brix (sweet) and relatively low acidity, excellent eating quality, and easy to eat fruits. In 2014, the second generation of the mother tree was grown by asexual reproduction by grafting onto a wild white-flowered peach tree rootstock (non-patented, being indigenous on a mountain in Tsukidate-cho, Date-city, Fukushima-prefecture, Japan), and the observation of the characteristics of the second generation tree was started. The asexually propagated tree remained true to the original tree (i.e., mother tree), and all characteristics of the tree and fruits of the mother tree were transmitted. In 2017, this new variety was denominated by the inventor as 'SWEET REI'.

The above-identified mother tree and the second generation tree of 'SWEET REI' have been maintained in Tsukidate-cho, Date-city, Fukushima-prefecture, Japan.

SUMMARY OF THE VARIETY

The new white nectarine variety 'SWEET REI' exhibits outstanding and distinguishing characteristics when grown under normal nectarine cultivation practices, including:

(1) high brix (Brix 15 to 17 degree), relatively low acidity, and white flesh fruit;
(2) excellent eating quality fruit;
(3) being easy to eat because of its freestone fruit;
(4) attractive dark-red fruit skin color; and
(5) no deterioration of eating quality of fruit even after storage for two weeks in a refrigerator.

The fruits of 'SWEET REI' is suitable for fruit gifts, such as fruit gift boxes or fruit baskets, since it has attractive dark-red skin color as well as excellent eating quality, and is easy to eat because of its freestone flesh.

In addition, since the fruit of 'SWEET REI' has high brix and relatively low acidity, it can also be used for preparation of processed fruits, such as fruit cake, fruit jelly, canned fruits, fruit juice and fruit jam.

For reliable description, the characteristics of 'SWEET REI' are described as compared to those of the yellow nectarine variety 'SWEET VENUS' (the seed parent of the present variety, *Prunus persica* (L.) Batsch var. *nucipersica* (Suckow) C.K. Schneid.) and the representative variety of white peach, 'Kawanakajima Hakuto' (*Prunus persica* (L.) Batsch), its the attached Table 1 (Table of Characteristics).

As stated herein below and described in the attached Table of Characteristics, 'SWEET REI' has apparently different characteristics from those of the variety 'SWEET VENUS' and the variety 'Kawanakajima Hakuto'.

'SWEET REI' clearly differs from its seed parent variety 'SWEET VENUS', which has yellow, relatively firm and clingstone fruits, in that 'SWEET REI' has dark-red fruit skin color, white fruit flesh, and relatively soft, freestone and easy to eat fruit. Moreover, since 'SWEET REI' needs not being grown under plastic cover, its cultivation is easier than that of 'SWEET VENUS', which needs to be plastic covered.

In addition, 'SWEET REI' clearly differs from the representative variety of white peach 'Kawanakajima Hakuto', which has Brix 13 degree, in that 'SWEET REI' has higher Brix (Brix 15 to 17 degree).

'SWEET REI' is in fact outstanding and readily identified as being such.

It should be noted that the plant age of all the plants of 'SWEET REI', which were observed and photographed for botanical description, was 3 years (except for the 7-year-old mother tree of 'SWEET REI' in FIG. 21).

DESCRIPTION OF THE DRAWINGS

This new white nectarine variety is illustrated by the accompanying digital color photographs, depicting defining characteristics of the plant by the best possible color photography. Colors of foliage, flowers, fruits and other plant parts may vary from year to year depending on, among other factors, nectarine cultivation practices, light conditions, air temperature, soil fertility, etc.

BOTANICAL DESCRIPTION OF THE VARIETY

Figure 1:
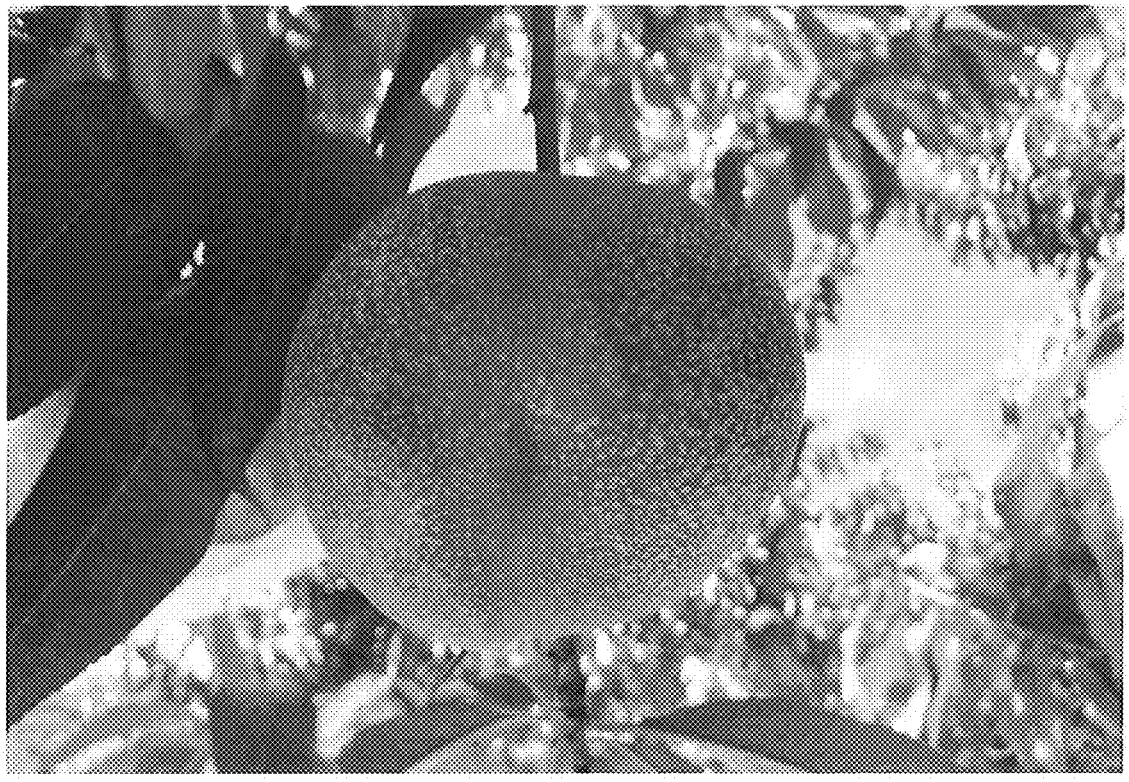
FIG. 1 illustrates a whole fruit of 'SWEET REI' fruiting on a tree (photographed date: Sep. 1, 2017; photographed location: Tsukidate-cho, Date-city, Fukushima-prefecture, Japan; and the age of photographed 'SWEET REI': 3 years).
Figure 2:
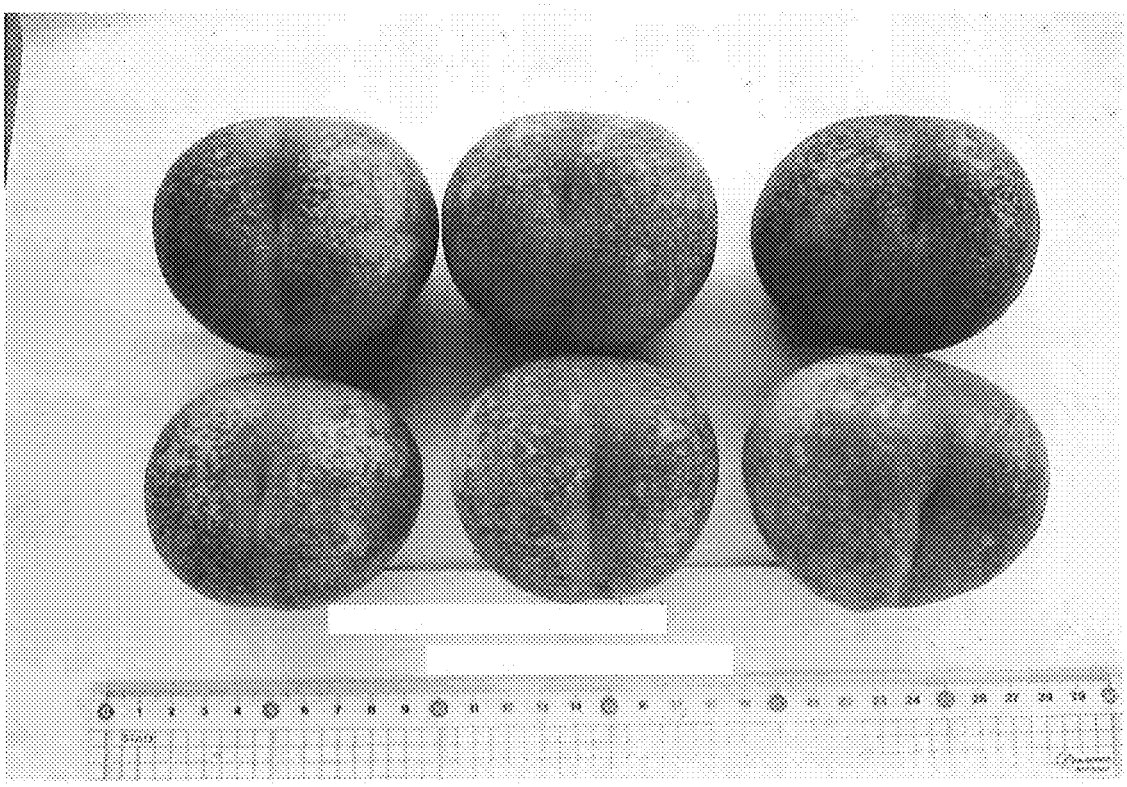
FIG. 2 illustrates apexes of 6 fruits of 'SWEET REI' (photographed date: Aug. 31, 2017; photographed location: Higashine-city, Yamagata-prefecture, Japan; and the age of photographed 'SWEET REI': 3 years).
Figure 3:
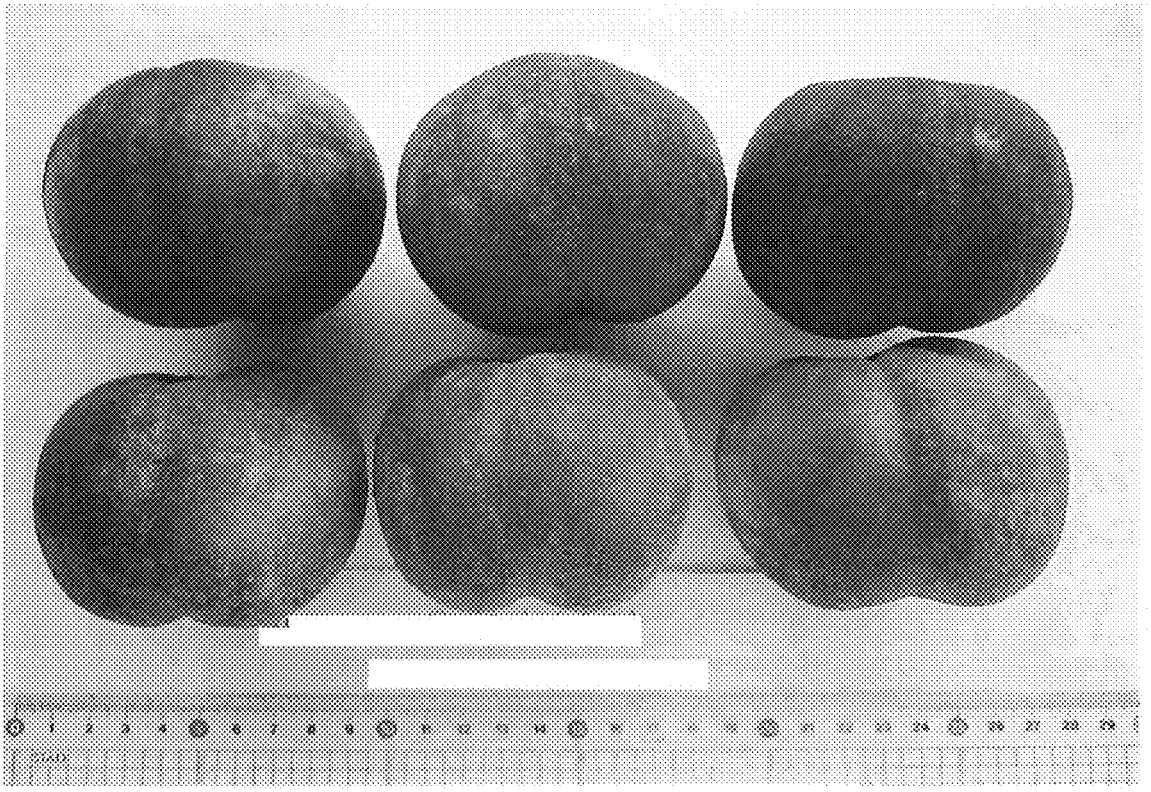
FIG. 3 illustrates lateral view of 6 fruits of 'SWEET REI' (photographed date: Aug. 31, 2017; photographed location: Higashine-city, Yamagata-prefecture, Japan; and the age of photographed 'SWEET REI': 3 years).
Figure 4:
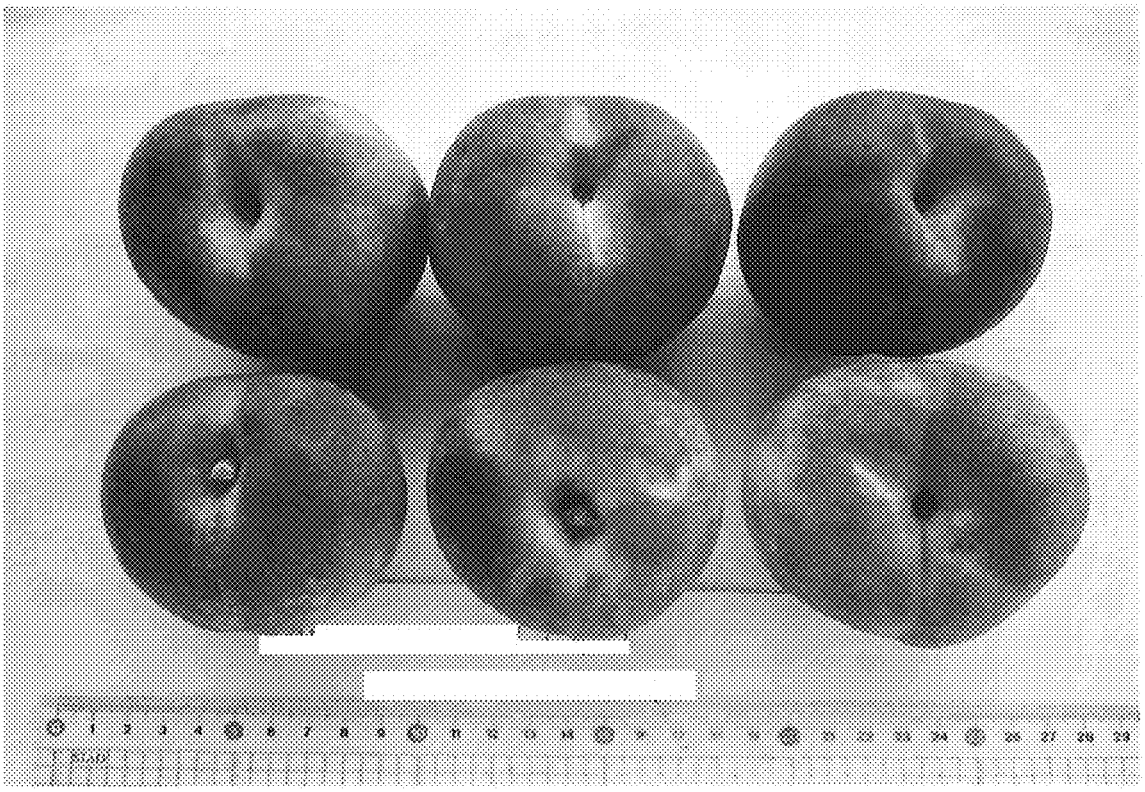
FIG. 4 illustrates stalk cavity of 6 fruits of 'SWEET REI' (photographed date: Aug. 31, 2017; photographed location: Higashine-city, Yamagata-prefecture, Japan; and the age of photographed 'SWEET REI': 3 years).
Figure 5:
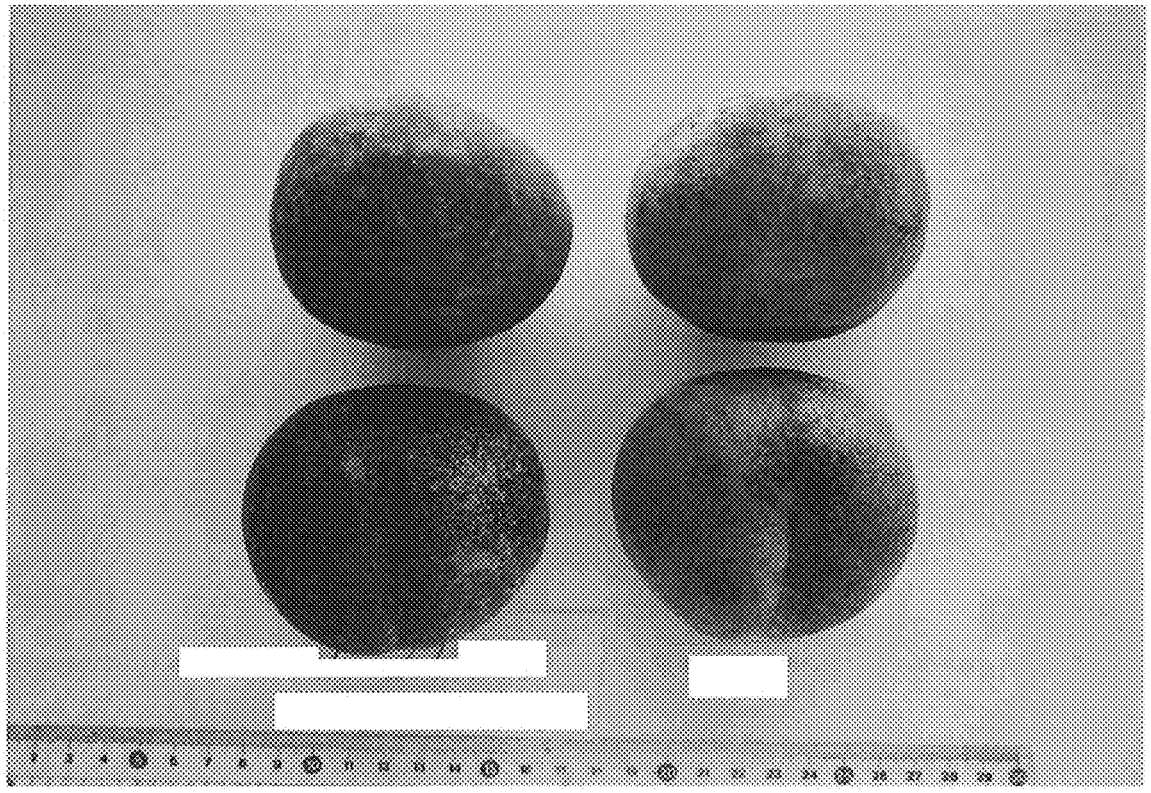
FIG. 5 illustrates 4 fruits of 'SWEET REI'; 2 bagged fruits (left) and 2 not bagged fruits (right) (photographed date: Sep. 1, 2017; photographed location: Higashine-city, Yamagata-prefecture, Japan; and the age of photographed 'SWEET REI': 3 years).
Figure 6:
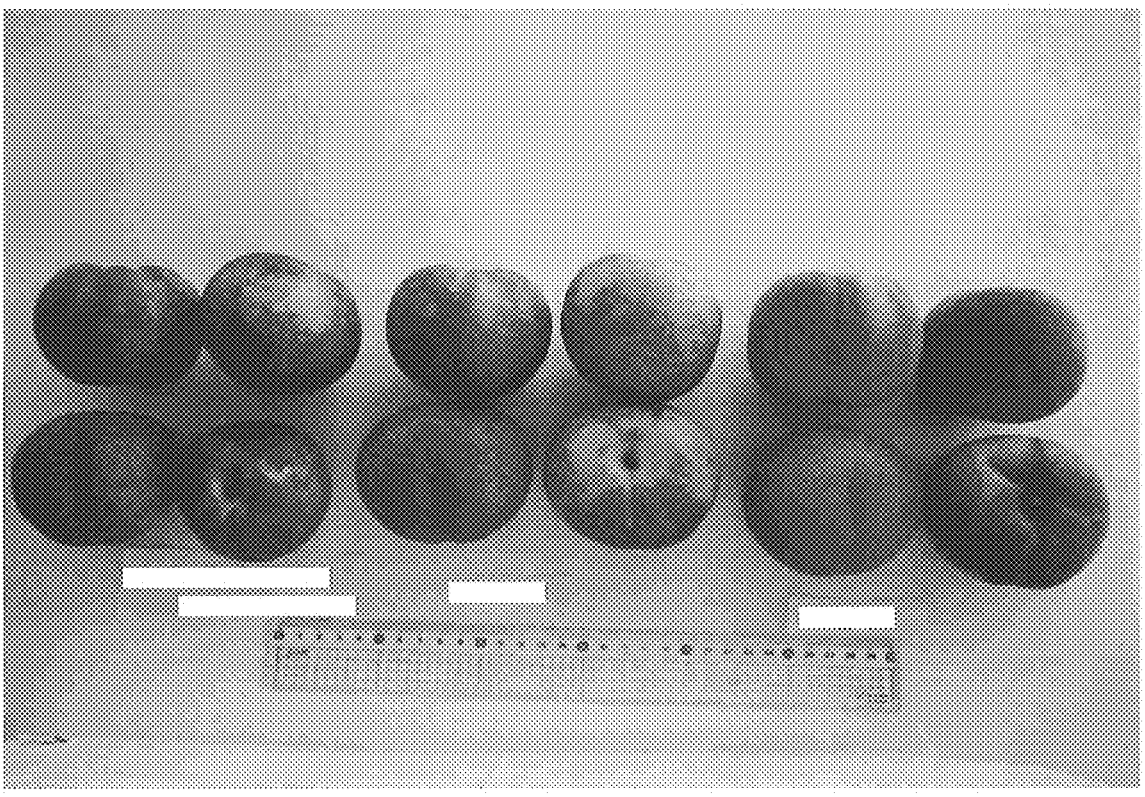
FIG. 6 illustrates 4 fruit of 'SWEET REI' (left), 'SWEET VENUS' (middle) and 'Kawanakajima Hakuto' (right), respectively (photographed date: Sep. 1, 2017; photographed location: Higashine-city, Yamagata-prefecture, Japan; and the age of photographed 'SWEET REI', 'SWEET VENUS' and 'Kawanakajima Hakuto': 3 years).
Figure 7:
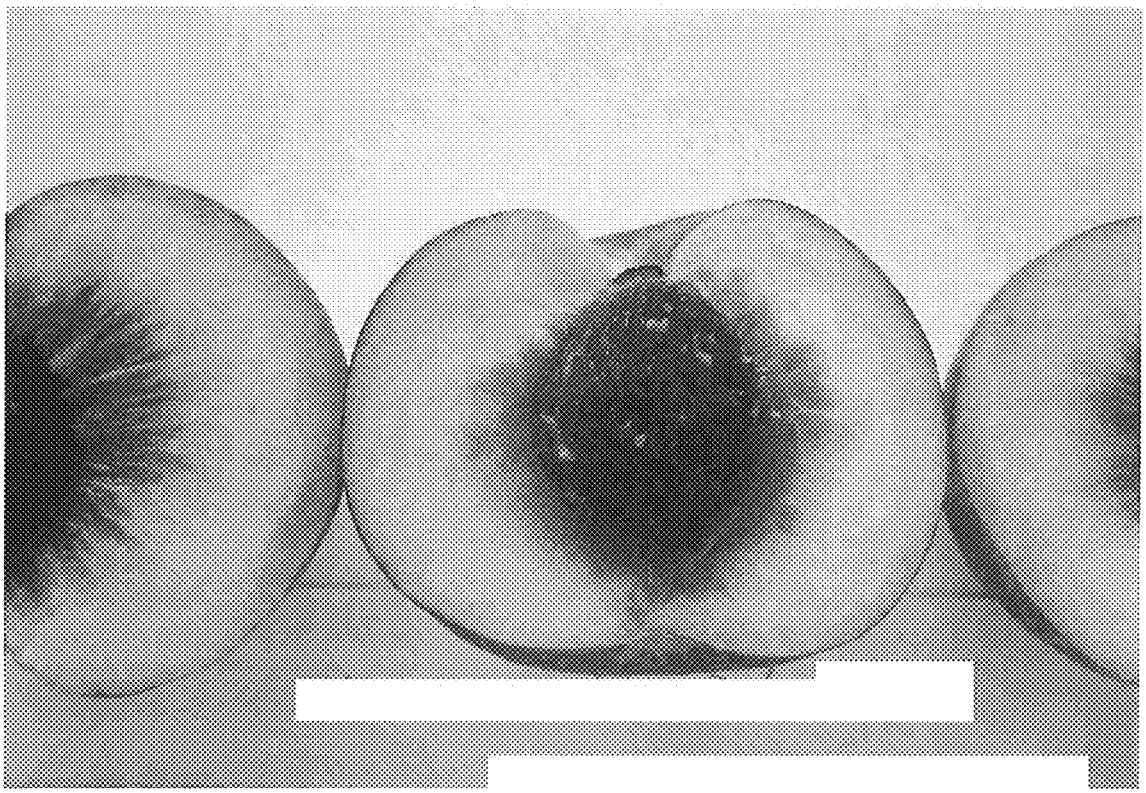
FIG. 7 illustrates longitudinal section view of fruits of 'SWEET REI' (photographed date: Aug. 31, 2017; photographed location: Higashine-city, Yamagata-prefecture, Japan; and the age of photographed 'SWEET REI'; 3 years).
Figure 8:
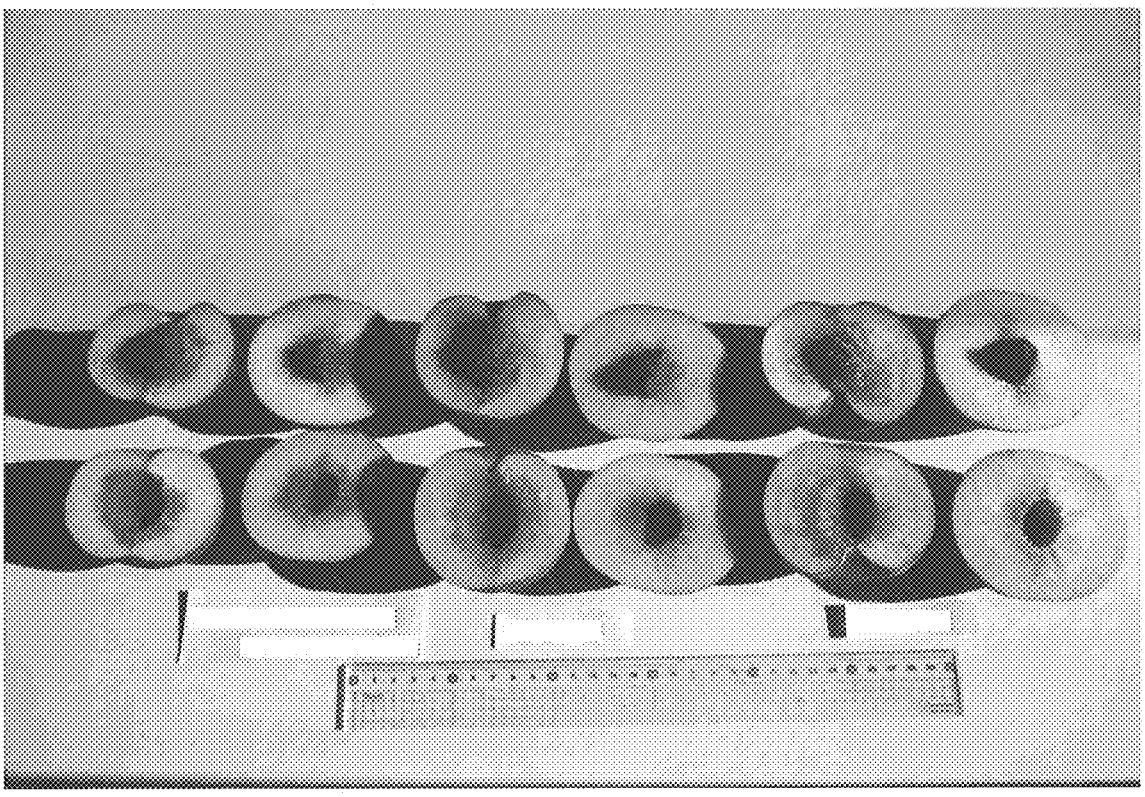
FIG. 8 illustrates cross section view of 4 fruits of 'SWEET REI' (left), 'SWEET VENUS' (middle) and 'Kawanakajima Hakuto' (right), respectively (photographed date: Sep. 1, 2017; photographed location: Higashine-city, Yamagata-prefecture, Japan; and the age of photographed 'SWEET REI', 'SWEET VENUS' and 'Kawanakajima Hakuto': 3 years).
Figure 9:
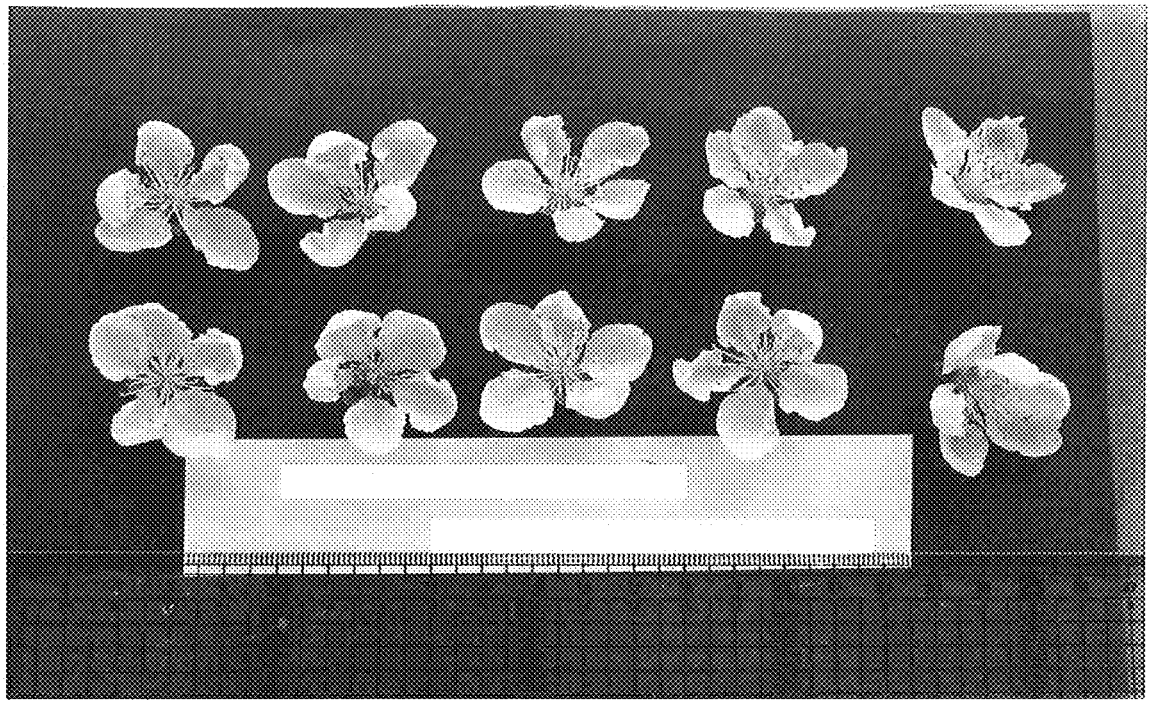
FIG. 9 illustrates 10 flowers of 'SWEET REI' (photographed date: Apr. 10, 2018; photographed location: Higashine-city, Yamagata-prefecture, Japan; and the age of photographed 'SWEET REI': 3 years).
Figure 10:
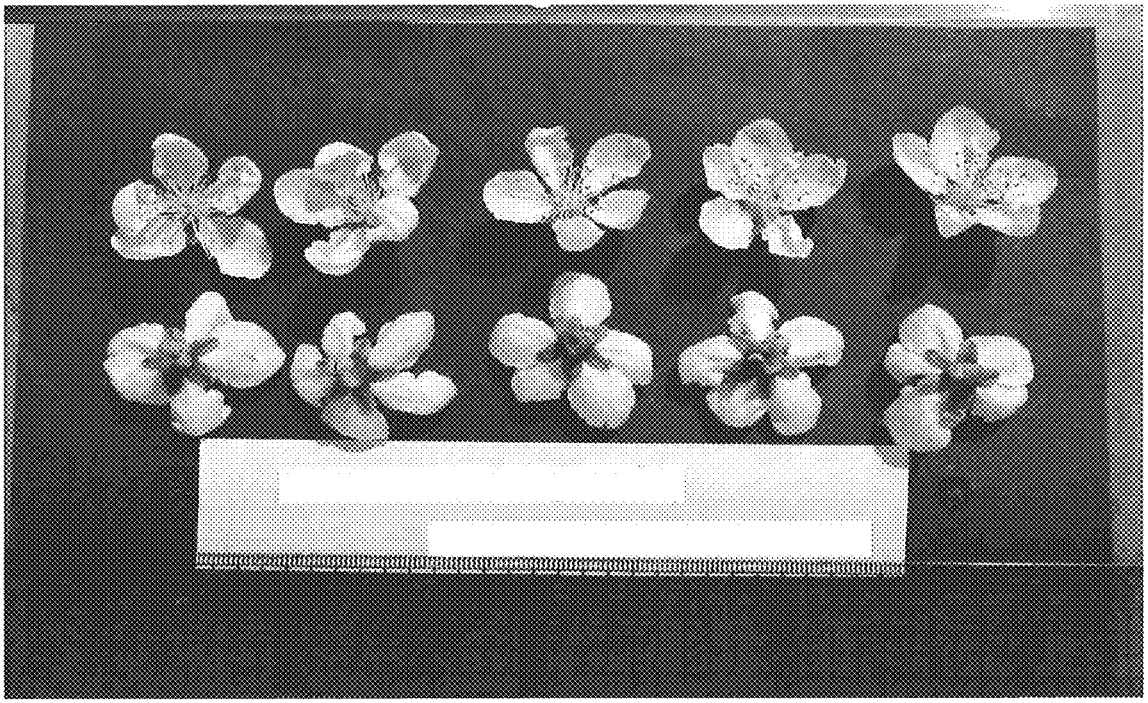
FIG. 10 illustrates 10 flowers of 'SWEET REI' (5 flowers before fertilization (upper) and 5 flowers with fertilized ovule (lower)) (photographed date: Apr. 10, 2018; photographed location: Higashine-city, Yamagata-prefecture, Japan; and the age of photographed 'SWEET REI': 3 years).
Figure 11:
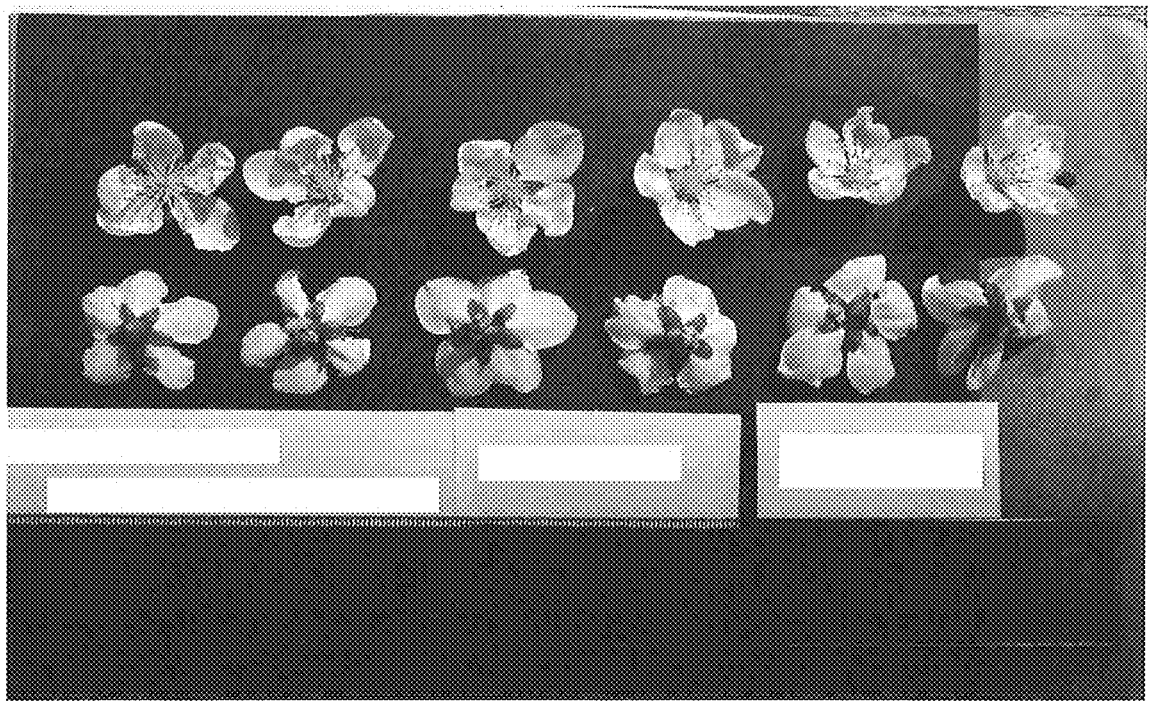
FIG. 11 illustrates 4 flowers of 'SWEET REI' (left), 'SWEET VENUS' (middle) and 'Kawanakajima Hakuto' (right), respectively (2 flowers before fertilization (upper) and 2 flowers with fertilized ovule (lower), respectively) (photographed date: Apr. 10, 2018; photographed location: Higashine-city, Yamagata-prefecture, Japan; and the age of photographed 'SWEET REI', 'SWEET VENUS' and 'Kawanakajima Hakuto': 3 years).
Figure 12:
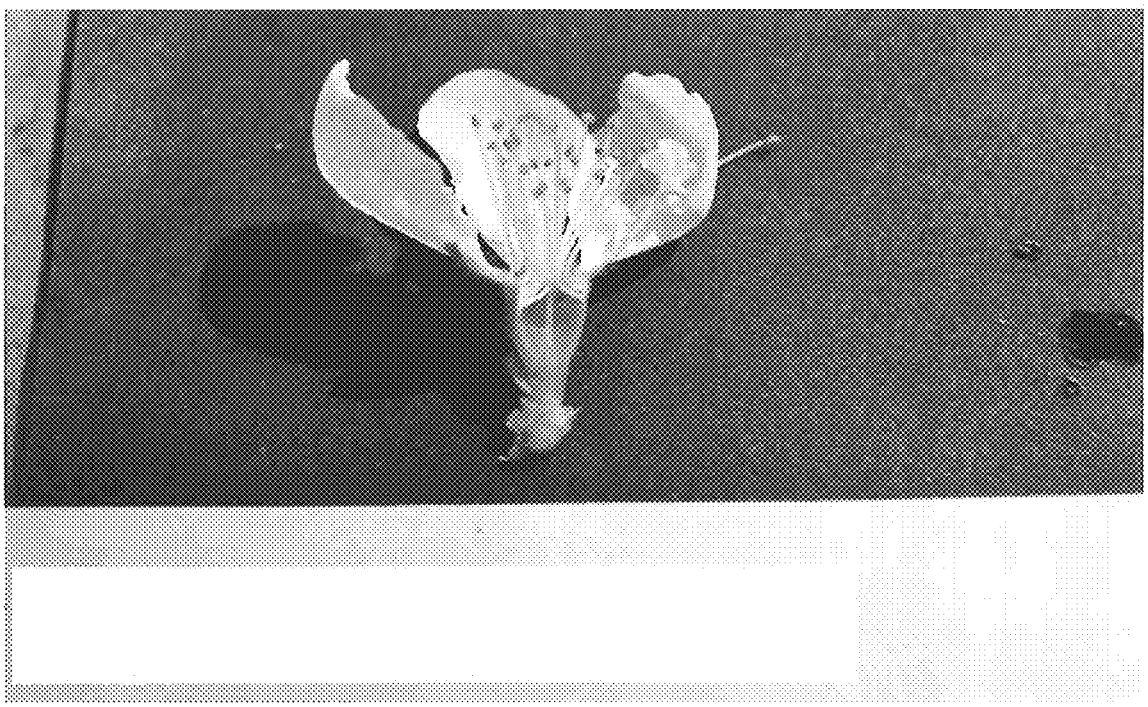
FIG. 12 illustrates a close-up longitudinal section view of a flower of 'SWEET REI' (photographed date: Apr. 10, 2018; photographed location: Higashine-city, Yamagata-prefecture, Japan; and the age of photographed 'SWEET REI': 3 years).
Figure 13:
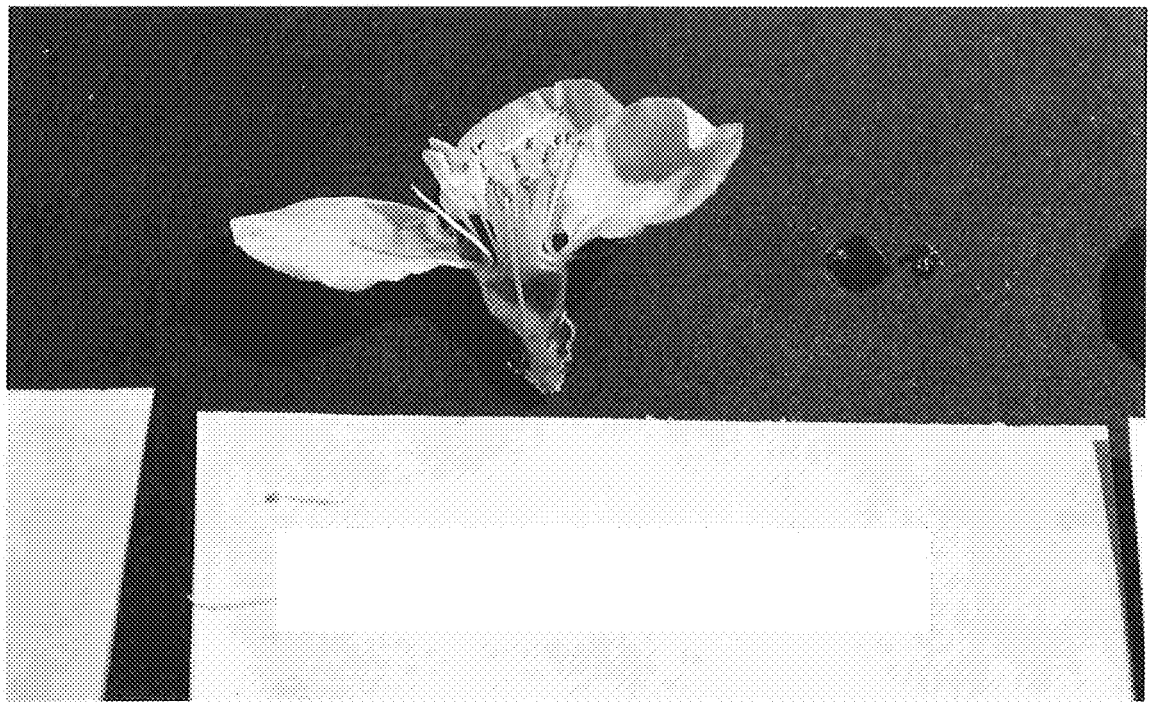
FIG. 13 illustrates a close-up longitudinal section view of a flower of 'SWEET VENUS' (photographed date: Apr. 10, 2018; photographed location: Higashine-city, Yamagata-prefecture, Japan; and the age of photographed 'SWEET REI': 3 years).
Figure 14:
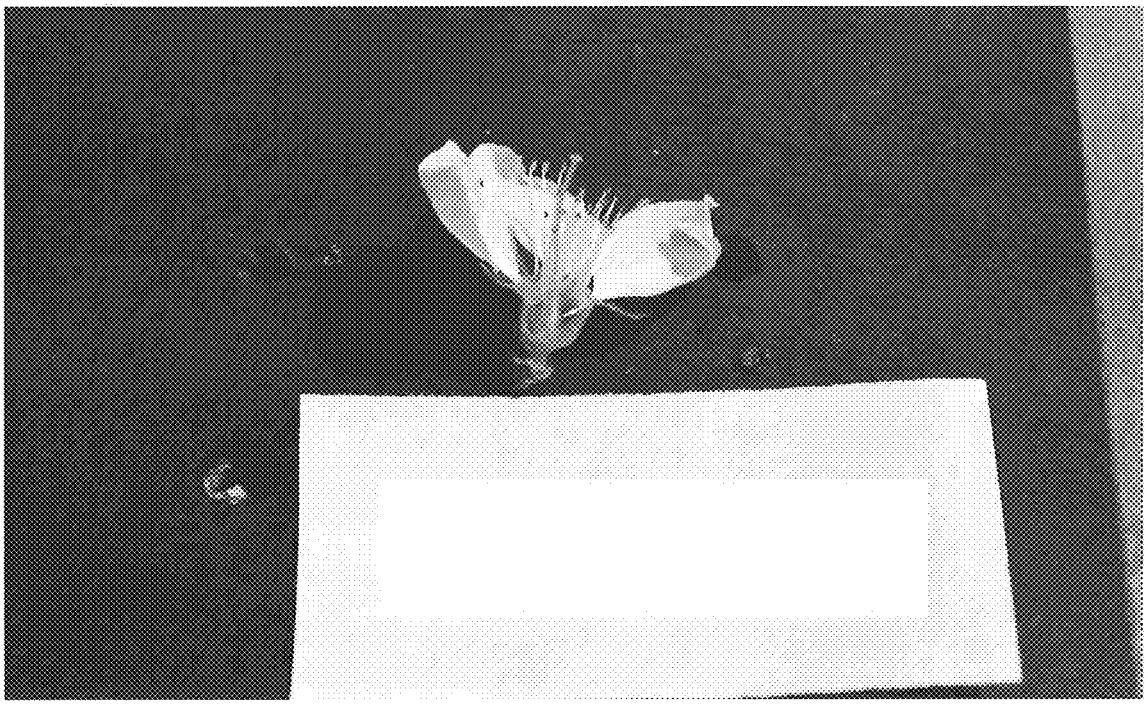
FIG. 14 illustrates a close-up longitudinal section view of a flower of 'Kawanakajima Hakuto' (photographed date: Apr. 10, 2018; photographed location: Higashine-city, Yamagata-prefecture, Japan; and the age of photographed 'SWEET REI': 3 years).
Figure 15:
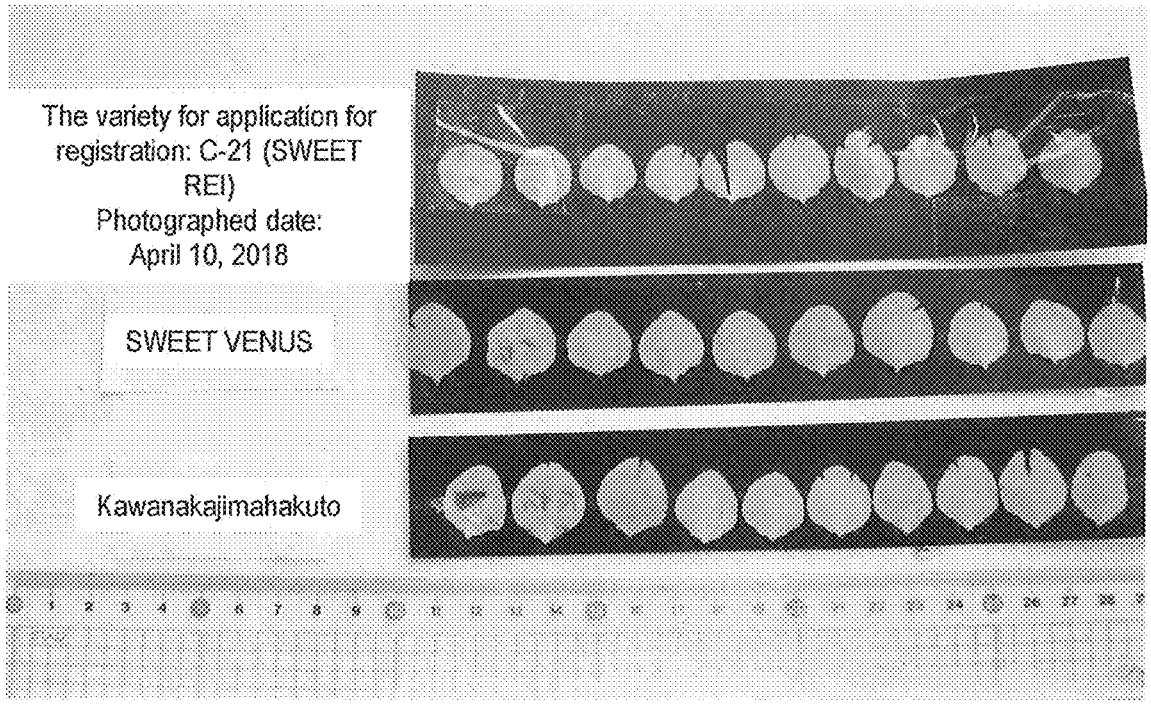
FIG. 15 illustrates 10 flower petals of 'SWEET REI' (upper), 'SWEET VENUS' (middle) and 'Kawanakajima Hakuto' (bottom), respectively (photographed date: Apr. 10, 2018; photographed location: Higashine-city, Yamagata-prefecture, Japan; and the age of photographed 'SWEET REI', 'SWEET VENUS' and 'Kawanakajima Hakuto': 3 years).
Figure 16:
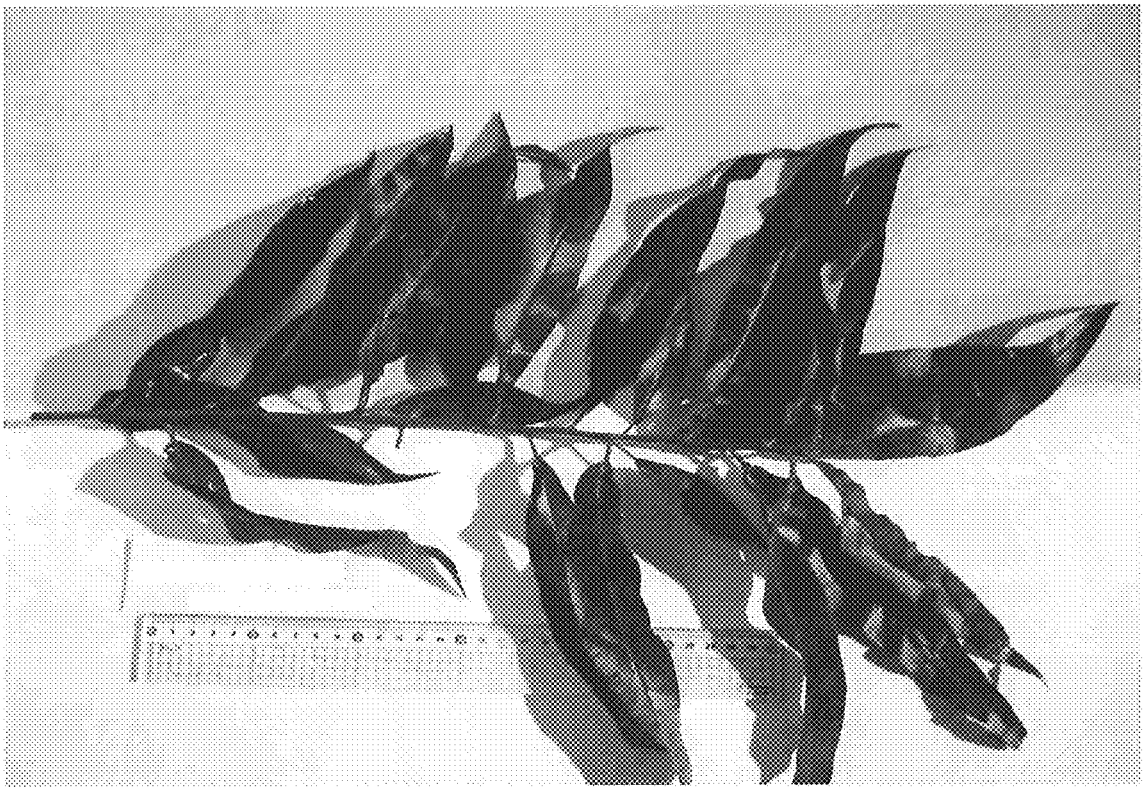
FIG. 16 illustrates a branch of 'SWEET REI' with a number of leaves (photographed date: Sep. 1, 2017; photographed location: Higashine-city, Yamagata-prefecture, Japan; and the age of photographed 'SWEET REI': 3 years).
Figure 17:
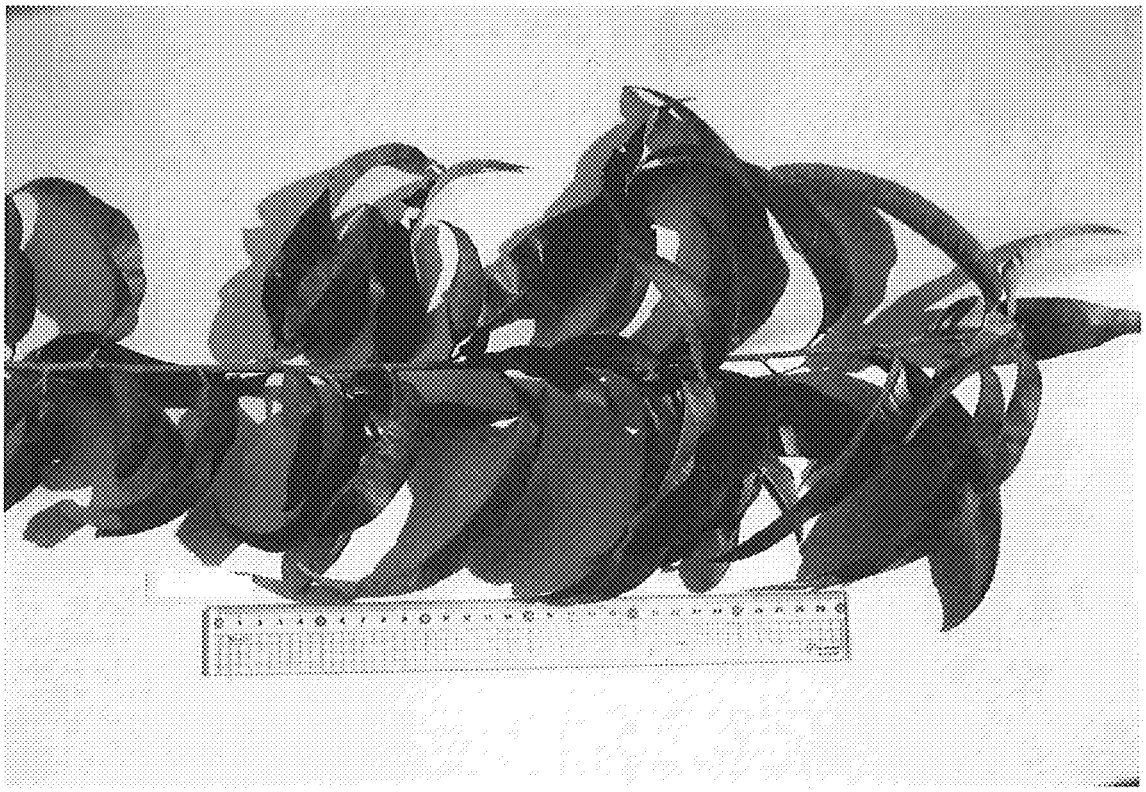
FIG. 17 illustrates a branch of 'SWEET VENUS' with a number of leaves (photographed date: Sep. 1, 2017; photographed location: Higashine-city, Yamagata-prefecture, Japan; and the age of photographed 'SWEET VENUS': 3 years).
Figure 18:
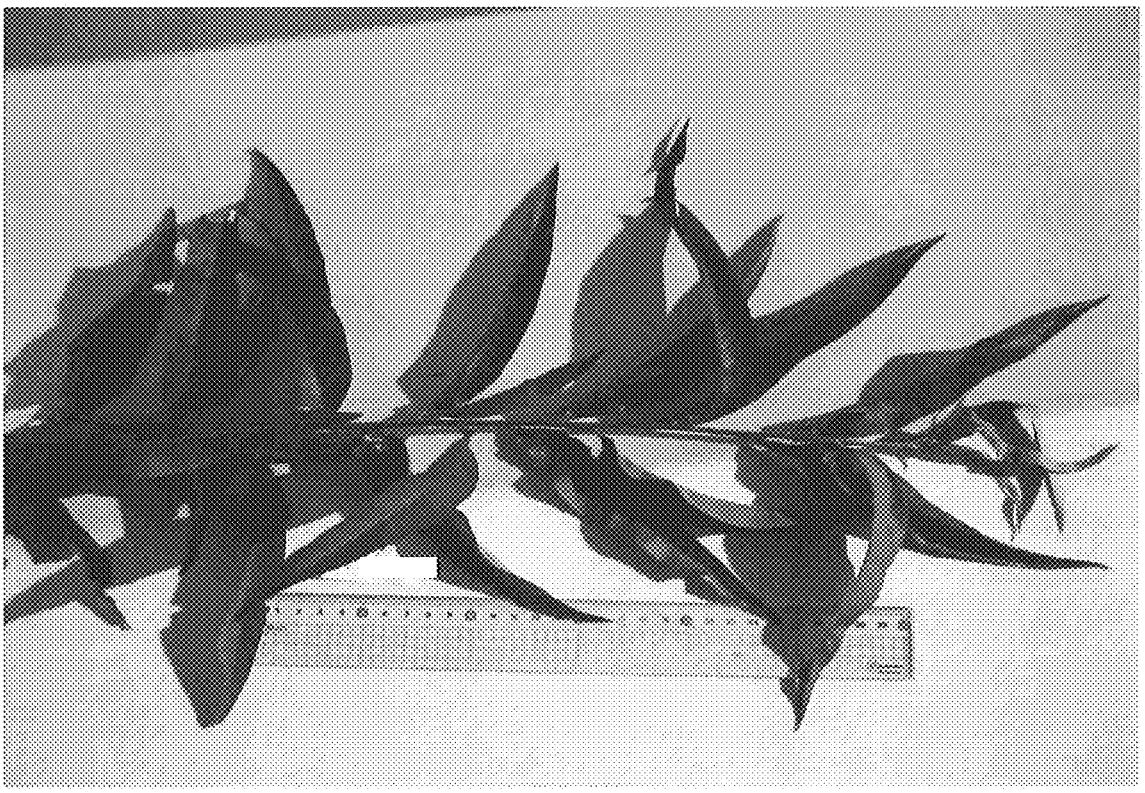
FIG. 18 illustrates a branch of 'Kawanakajima Hakuto' with a number of leaves (photographed date: Sep. 1, 2017; photographed location: Higashine-city, Yamagata-prefecture, Japan; and the age of photographed 'Kawanakajima Hakuto': 3 years).
Figure 19:
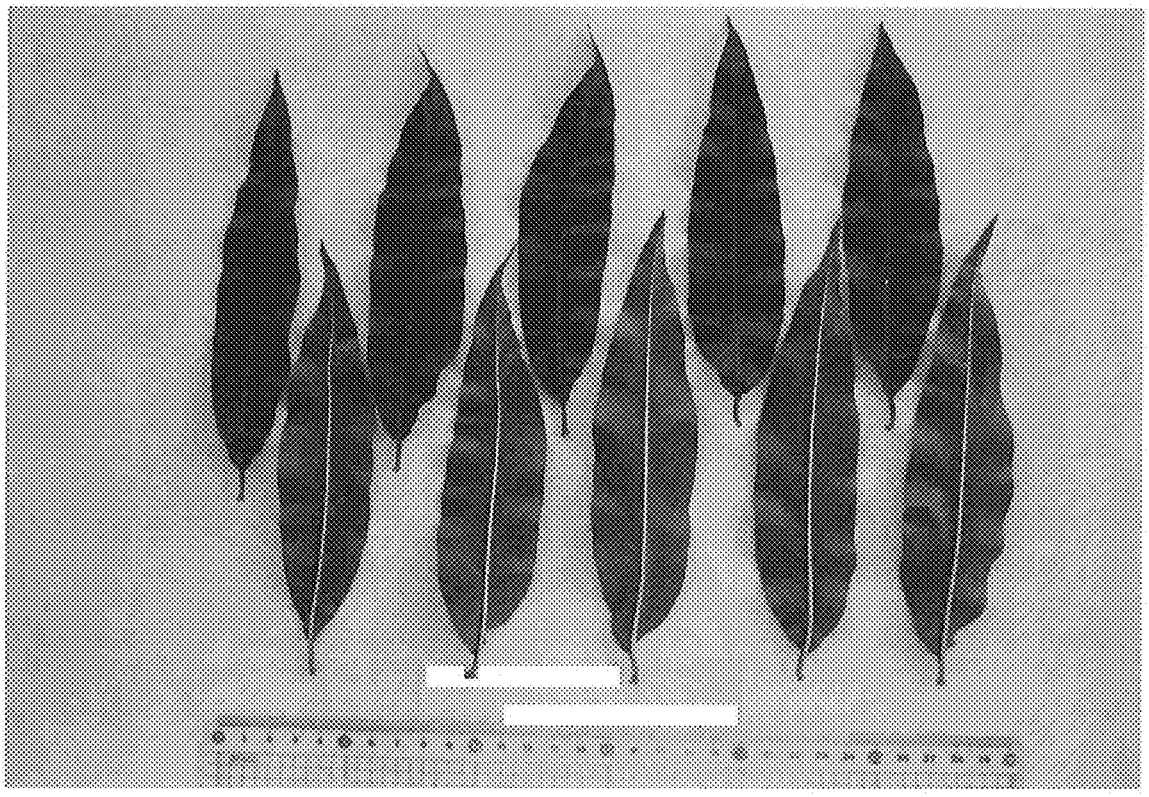
FIG. 19 illustrates 10 leaves of 'SWEET REI' (5 upper surface of leaves (upper) and 5 lower surface of leaves (lower)) (photographed date: Sep. 1, 2017; photographed location: Higashine-city, Yamagata-prefecture, Japan; and the age of photographed 'SWEET REI': 3 years).
Figure 20:
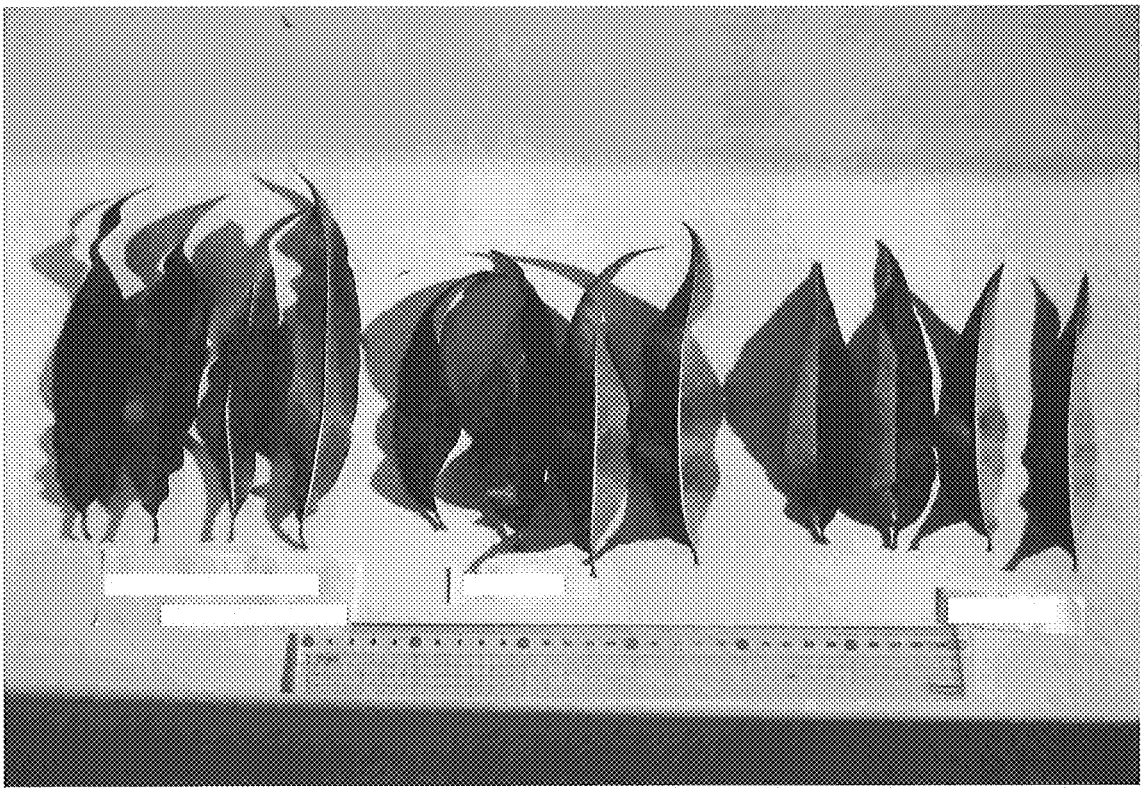
FIG. 20 illustrates 4 leaves of 'SWEET REI' (left), 'SWEET VENUS' (middle) and 'Kawanakajima Hakuto' (right), respectively (2 upper surface of leaves (left), and 2 lower surface of leaves (right), respectively) (photographed date: Sep. 1, 2017; photographed location: Higashine-city, Yamagata-prefecture, Japan; and the age of photographed 'SWEET REI', 'SWEET VENUS' and 'Kawanakajima Hakuto': 3 years).
Figure 21:
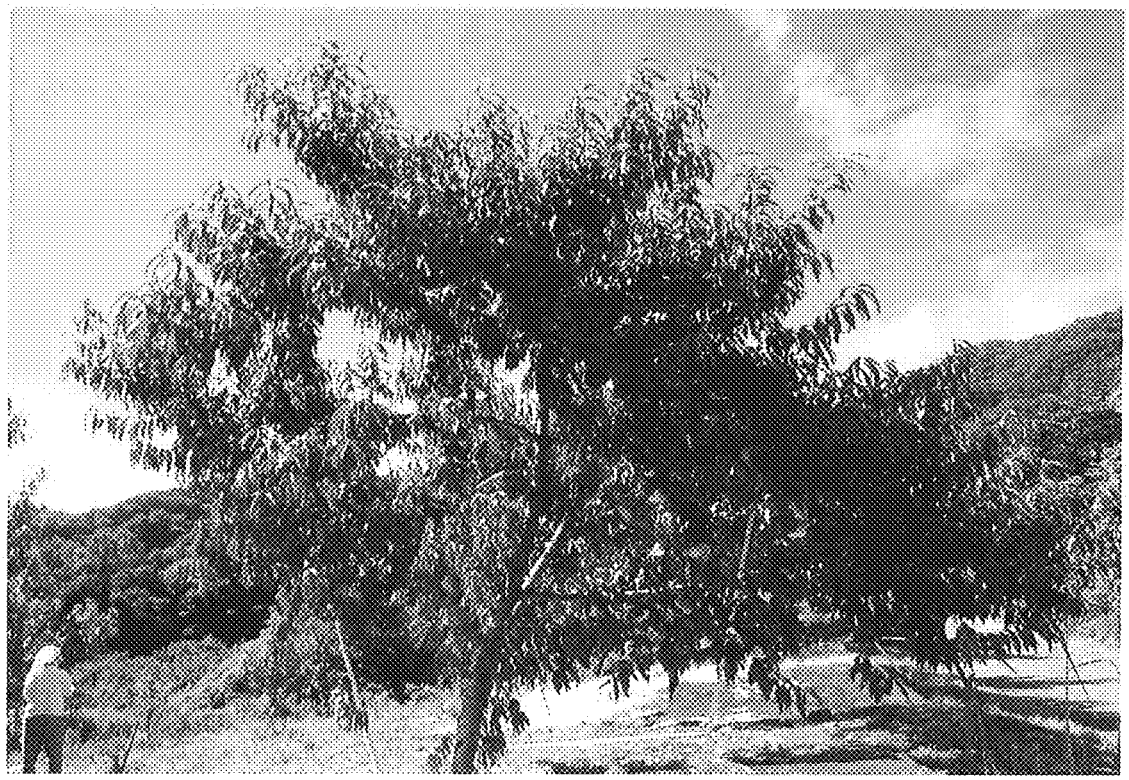
FIG. 21 illustrates a whole mother tree of 'SWEET REI' (photographed date: Sep. 1, 2017; photographed location: Tsukidate-cho, Date-city, Fukushima-prefecture, Japan; and the age of photographed 'SWEET REI': 7 years).

The following is a detailed botanical description of the new variety of white nectarine, its tree, flower, foliage and fruit, as based on observations of 3 year old specimens grown in Tsukidate-cho, Date-city, Fukushima-prefecture, Japan, with color in accordance with The R.H.S. Colour Chart 2015.

1. Tree:
   - *Size*.—Medium (3 year old tree: Height: 5 to 3 m; Width: 3.5 to 4 m).
   - *Vigor*.—Medium vigorous.
   - *Growth habit*.—Semi-upright.
   - *Tree shape*.—Flared shape.
   - *Hardiness*.—USDA hardiness zone 8a.
   - *Disease pest resistance/susceptibility*.—Resistance to *Xanthomonas arboricola* pv. *pruni*.
   - *Trunk diameter* (*at 50 cm height from ground*).—18.9 cm.
   - *Bark texture*.—Smooth (8 year old tree).
   - *Bark color*.—Gray (RHS Code: 201D).
   - *Trunk lenticel number*.—0.7/cm$^2$.
   - *Trunk lenticel shape*.—Long ellipse.
   - *Trunk lenticel height*.—1.5 mm.
   - *Trunk lenticel width*.—3.0 mm.
   - *Trunk lenticel color*.—Gray-brown (RHS Code: N119C).
2. Shoot:
   - *Shoot length*.—22.0 cm.
   - *Shoot diameter*.—0.3 cm.
   - *Shoot texture*.—Smooth.
   - *Shoot internode length*.—2.4 cm.
   - *Shoot color*.—Green (RHS Code: 142C).
3. Leaves:
   - *Time of leaf bud burst*.—Medium, around March 25 (3 year old tree).
   - *Leaf blade shape*.—Lanceolate.
   - *Leaf blade length*.—Average length 18.61 cm.
   - *Leaf blade width*.—Average width 3.71 cm.
   - *Leaf ratio of length/width*.—Large (average 5.02).
   - *Leaf blade shape in cross section*.—Flat.
   - *Leaf apex form*.—Attenuate-acuminate.
   - *Leaf margin*.—Sawtoothed.
   - *Recurvature of leaf blade apex*.—Absent.
   - *Shape* (*angle*) *at base of leaf blade*.—Acute.
   - *Leaf texture*.—Smooth and glabrous on both surfaces.
   - *Color of upper surface of mature leaf blade*.—Dark Green (RHS Code: 136A).
   - *Color of lower surface of mature leaf blade*.—Strong Yellow Green (RHS Code: 144A).
   - *Leaf venation pattern*.—Pinnately veined, and having concavo-convex veins on lower surface of leaves.
   - *Red mid-vein on lower surface of mature leaf blade*.—Absent.
   - *Petiole length*.—Average length 1.34 cm.
   - *Petiole diameter*.—2 mm.
   - *Petiole texture*.—Smooth.
   - *Color of petiole*.—Green (RHS Code: 142C).
   - *Nectaries on petiole of leaf*.—Present.
   - *Shape of nectaries on petiole of leaf*.—Rounded and reniform.
   - *Predominant number of nectaries on petiole of leaf*.—More than two.
4. Flower buds:
   - *Density of flower buds on the first-year flowering shoot*.—Dense.
   - *General distribution of flower buds on the first-year flowering shoot*.—Distributed in groups of two or more.
   - *Flower bud shape*.—Conic in form with a round tip.
   - *Flower bud length*.—7.3 mm.
   - *Flower bud diameter*.—3.9 mm.
   - *Flower bud color*.—Light Greenish Grey (RHS Code: 188C).
5. Flowers:
   - *Flower type*.—Showy.
   - *Flower height*.—26 mm.
   - *Flower diameter*.—35 mm.
   - *Flower fragrance*.—Faint.
   - *Calyx color of inner side* (*opened flower, before falling of petals*).—Strong Yellowish Green (RHS Code: N144A).
   - *Corolla: predominant color* (*inner side*).—Light Purplish pink (RHS Code: 65B).
   - *Petal shape*.—Rounded shaped.
   - *Petal size*.—Average size 3.27 cm$^2$.
   - *Petal length*.—17 mm.
   - *Petal width*.—15 mm.
   - *Petal number per flower*.—Five.
   - *Petal apex*.—Rounded and curved.
   - *Petal margin*.—Undulating like a wave.
   - *Petal base*.—Acute.
   - *Petal texture*.—Smooth and soft (both surfaces).
   - *Sepal number per flower*.—Five.
   - *Sepal length*.—8 mm.

*Sepal width.*—4 mm.
*Sepal shape.*—Conic with a round tip.
*Sepal apex.*—Rounded.
*Sepal margin.*—Smooth.
*Color of upper surface of sepal.*—Red Purple (RHS Code: 59C).
*Color of lower surface of sepal.*—Green (RHS Code: 141C).
*Time of beginning of flowering.*—Medium, around April 12 (3 year old tree).
*Duration of flowering.*—Medium, around April 12 to around April 24 (3 year old tree).

6. Reproductive organs:
*Stamens position compared to petals.*—Below.
*Stamen number.*—41.
*Stigma position compared to anthers.*—Above.
*Anther length.*—1 mm.
*Color of anther.*—Yellow Orange (RHS Code: 20A).
*Filament length.*—12 mm.
*Color of filament.*—Red Purple (RHS Code: 68B).
*Pistil number.*—One (1).
*Pistil length.*—19 mm.
*Pollen in anthers.*—Present.
*Pollen amount.*—Abundant.
*Color of pollen.*—Yellow Orange (RHS Code: 22B).
*Pubescence on ovary.*—Absent.

7. Fruit:
*Fruit size (weight).*—Medium, Average weight: 208.7 g.
*Fruit shape in ventral view.*—Oblate.
*Fruit shape of pistil end.*—Weakly depressed.
*Fruit: symmetry viewed from pistil end.*—Asymmetric.
*Fruit cheek diameter.*—81.0 to 85.0 mm.
*Fruit axial diameter.*—10.0 to 72.0 mm.
*Fruit: prominence of suture.*—Medium.
*Fruit: depth of stalk cavity.*—Medium, Average depth: 1.3 cm.
*Fruit: width of stalk cavity.*—20 mm.
*Fruit: ground color of fruit skin.*—Light Yellow Green (RHS Code: 54D).
*Presence or absence of over color of fruit skin.*—Present.
*Fruit: hue of over color of fruit skin.*—Dark Red (RHS Code: 59A).
*Fruit: pattern of over color of fruit skin.*—Mottled.
*Fruit: extent of over color of fruit skin (bagged fruit).*—100%.
*Fruit: extent of over color of fruit skin (non-bagged fruit).*—50%.
*Pubescence on fruit.*—Absent.
*Fruit: thickness of skin.*—Thin.
*Fruit: adherence of skin to flesh.*—Strong.
*Fruit: firmness of flesh.*—Medium.
*Fruit: ground color of fruit flesh.*—Yellowish White (RHS Code: 155B).
*Fruit: anthocyanin coloration directly under fruit skin.*—Absent or very weakly expressed.
*Color of anthocyanin coloration directly under fruit skin, very weakly expressed.*—Red Purple (RHS Code: 58B).
*Fruit: anthocyanin coloration of fruit flesh.*—Absent or very weakly expressed.
*Color of anthocyanin coloration of fruit flesh, when very weakly expressed.*—Red Purple (RHS Code: N66C).
*Fruit: anthocyanin coloration around stone.*—Strongly expressed.
*Color of anthocyanin coloration around stone.*—Red Purple (RHS Code: N57B).
*Fruit: texture of fruit flesh.*—Not fibrous.
*Fruit sweetness.*—High, Brix 15 to 17 degree.
*Fruit acidity.*—Medium.
*Fruit taste.*—Sweet, high level of sugars and relatively low acidity.
*Fruit eating quality.*—Very good and easy to eat.
*Time of maturity for consumption.*—Late, around late August.
*Tendency to crack.*—Present.
*Tendency to preharvest drop.*—Weak.
*Date of first picking.*—Around August 25.
*Date of last picking.*—Around September 5.
*Productivity.*—Around 600 fruits are produced per tree per season (8 year old tree).

8. Stone:
*Stone: size compared to fruit (ratio weight of stone/weight of fruit).* Small.
*Stone length.*—34 mm.
*Stone width.*—22 mm.
*Stone diameter.*—27 mm.
*Stone shape in lateral view.*—Obovate.
*Stone apex shape.*—Short, pointed.
*Stone base shape.*—Straight.
*Stone: intensity of brown color.*—Dark.
*Stone: relief of surface.*—Pits and grooves.
*Stone: tendency of splitting (at peak harvest)).*—Medium.
*Stone: presence or absence of adherence to fruit flesh.*—Absent.
*Stone: degree of adherence to flesh.*—Weak.
*Stone cavity: length.*—23 mm.
*Stone cavity: diameter.*—13 mm.
*Kernel length.*—17 mm.
*Kernel width.*—12 mm.
*Kernel thickness.*—5 mm.
*Kernel shape.*—Long elliptic.
*Color of kernel.*—Grayed Orange (RHS Code: 172C).

9. Others:
*Keeping quality.*—Remarkable. Fruit of 'SWEET REI' have a slow maturation and a long shelf life both on the tree after growth completion (before harvesting) and after harvesting without alteration. After harvest, fruits are well preserved around 2 weeks, at around 4.0 degree Celsius.
*Shipping quality.*—Considered very good. The fruits of 'SWEET REI' showed minimal bruising of the flesh or skin damage after being subjected to normal harvesting and packing procedures. Its resistance to handling during harvest and packing and its long shelf life without alteration after harvest easily permit around 2 weeks-shipping, at around 4.0 degrees Celsius.

The comparison of characteristics of the present variety 'SWEET REI' with the comparator varieties 'SWEET VENUS' and 'Kawanakajimahakuto' is summarized in Table 1 below.

TABLE 1

(Table of Characteristics)

| Character No. | UPOV No. | Symbol | Characteristics | |
|---|---|---|---|---|
| 1 | 10 | QNG | Tree: size | |
| 2 | 2 | QN | Tree: vigor | |
| 3 | 3(*) | QN | Tree: habit | |
| 4 | 4 | QN | Flowering shoot: thickness (excluding brindilles) | |
| 5 | 5 | QN | Flowering shoot: length of internodes (excluding brindilles) | |
| 6 | 6(*) | QL | Flowering shoot: anthocyanin coloration (excluding brindilles, side away from sun) | |
| 7 | 7(*) | QN | Flowering shoot: intensity of anthocyanin coloration (excluding brindilles, side away from sun) | |
| 8 | 8(*) | ON | Flowering shoot: densly of flower buds | |
| 9 | 9 | QL | Flowering shoot: general distribution of flower buds (excluding brindilles, side away from sun) | |
| 10 | 10(*) | QLG | Flower type | |
| 11 | 11(*) | PQ | Calyx color of inner side (opened flower, before falling of petals) | |
| 12 | 12(*) | PQ | Corolla: predominant color (inner side) | |
| 13 | 13(*) | PQ | Petal: shape | |
| 14 | 14(*) | QN | Petal: size | |
| 15 | 15(*) | QL | Petals: number | |
| 16 | 16 | QN | Stamens; position compared to petals | |
| 17 | 17(*) | QN | Stigma: position compared to anthers | |
| 18 | 18(*) | QL | Anthers: pollen | |
| 19 | 19(*) | QL | Ovary: pubescence | |
| 21 | 21(*) | QN | Leaf blade: length | |
| 22 | 22(*) | QN | Leaf blade: width | |
| 23 | 23(*) | QN | Leaf blade , ratio length/width | |
| 24 | 24 | PQ | Leaf blade: shape in cross section | |
| 25 | 25 | QL | Leaf blade: recurvature of apex | |
| 26 | 26 | PQ | Leaf blade angle at base | |
| 28 | 28 | PQ | Leaf blade: color | |
| 29 | | QL | Leaf: red mid-vein on the lower side | |
| 30 | 29 | QN | Petiole: lenglh | |
| 31 | 30(*) | QLG | Petiole: nectaries | |
| 32 | 31(*) | PG(*) | Petiole: shape of nectaries | |
| 33 | 32 | QL | Petiole: predominant number of nectaries | |
| 34 | 33(*) | QN | Fruit: size | |
| 35 | 34(*) | PQ(+) | Fruit: shape (in ventral view) | |
| 36(*) | 35 | PG | Fruit: shape of pistil end | |
| 37 | 36 | QL(+) | Fruit: symmetry (viewed from pistil end) | |
| 38 | 37 | QN | Fruit: prominence of suture | |
| 39 | 38 | QN(+) | Fruit: depth of stalk cavity | |
| 40 | 39 | QN | Fruit: width of stalk cavity | |
| 41 | 40(*) | PQ | Fruit: groundcolor | |
| 42 | 41 | QL | Fruit: over color | |
| 43 | 42 | PQ | Fruit: hue of over color | |
| 44 | 43(*) | PQ | Fruit : pattern of over color | |
| 45 | 44(*) | QN | Fruit: extent of over oobr | |
| 46 | 45(*) | QIG | Fruit: pubescence | |
| 48 | 47 | QN | Fruit: thickness of skin | |
| 49 | 48 | QN | Fruit: adherence of skin to flesh | |
| 50 | 49(*) | QN | Fruit: firmness of flesh | |
| 51 | 50(*) | PQG | Fruit: ground colorof flesh | |
| 52 | 51(*) | QN | Fruit: anthocyanin coloration directly under skin | Fruit: anthocyanin coloration directly under skin |
| 53 | 52(*) | QN | Fruit: anthocyanin coloration of flesh | Fruit: anthocyanin coloration of flesh |
| 54 | 53(*) | QN | Fruit: anthocyanin coloration around stone | Fruit: anthocyanin coloration around stone |
| 55 | 54 | QL | Fruit: texture ot the flesh | Fruit: texture of the flesh |
| 56 | 55 | QN | Fruit: sweetness | Fruit: sweetness |
| 57 | 56 | QN | Fruit: acidity | Fruit: acidity |
| 58 | 57(*) | QN | Stone: size compared to fruit | Stone: size compared to fruit |
| 59 | 58(*) | PQ(*) | Stone: shape in lateral view | Stone: shape (in lateral view) |
| 60 | 59 | ON | Stone: intensity of brown color | Stone: intensity of brown color |
| 61 | 60 | PC(*) | Stone: relief of surface | Stone, relief of surface |
| 62 | 61 | QN | Stone: tendency of splitting | Stone: tendency of splitting (at peak harvest) |
| 63 | 62(*) | QLG | Stone: adherence to flesh | Stone: adherence to flesh |
| 64 | 63 | ON | Stone: degree of adherence to flesh | Stone: degree of adherence to flesh |
| 65 | 64 | QN | Tine of leaf bud burst | Time of leaf bud burst |
| 66 | 65(*) | QNG | Tine of beginning of flowering | Time of beginning of flowering |
| 67 | 66(*) | QN | Duration of flowering | Duration of flowering |
| 68 | 67(*) | QNG | Time of maturity tor consumption | Time of maturity for consumption |
| 69 | 68 | QN | Tendency to preharvest drop | Tendency to preharvest drop |

TABLE 1-continued (Table of Characteristics)

| Character No. | Definition | Method | Grade |
|---|---|---|---|
| 1 | Size of whole tree | Observation | 1<br>3<br>5<br>6<br>7<br>9 |
| 2 | Vigor of growth of branches | Observation | 3<br>5<br>7 |
| 3 | Shape of whole tree, viewed from lateral side | Observation | 1<br>3<br>5<br>7<br>9 |
| 4 | Thickness of center part of first-year grown shoot | Measurement mm | 3<br>5<br>7 |
| 5 | Length of internodes of center part of first-year grown shoot | Measurement cm | 1<br>3<br>5<br>7<br>9 |
| 6 | Presence or absence of anthocyanin expression in first-year flowering shoot, side away from sun | Observation | 1<br>9 |
| 7 | Intensity of anthocyanin expression in a first-year flowering shoot | Observation | 3<br>6<br>7 |
| 8 | Density of fbwer buds on a first-year flowering shoot | Measurement | 3<br>5<br>7 |
| 9 | General distrimtbn of flower buds on a first-year flowering shoot | Observation | 1<br>2 |
| 10 | Flower type in flowering time | Observation | 1<br>2 |
| 11 | Color of inner side of calyx-tube in flowering time | Observation | 1<br>2 |
| 12 | Color of inner | Observation | 1 |

TABLE 1-continued (Table of Characteristics)

| | | | |
|---|---|---|---|
| | side of petal in flowering time | | 2<br>3<br>4<br>5<br>6<br>7 |
| 13 | Shape of petal in flowering time | Observation | 1<br>2<br>3 |
| 14 | Size of petal in flowering tine | Measurement cm | 1<br>3<br>5<br>7<br>9 |
| 15 | Number of petals per flower in flowering time | Measurement | 1<br>2 |
| 16 | Relative position of stamens to petals in flowering time | Observation | 1<br>2<br>3 |
| 17 | Relative position of stigma to antoers in flowering time | Observation | 1<br>2<br>3 |
| 18 | Presence or absence of pollen in flowering time | Observation | 1<br>9 |
| 19 | Presence or absence of pubescence on ovary in flowering time | Observation | 1<br>9 |
| 21 | Longitudinal length of mature leaf on center part of first-year shoot (excluding petiole) | Measurement cm | 3<br>5<br>7 |
| 22 | Maximum width of mature leaf on center part of first-year shoot | Measurement cm | 3<br>5<br>7 |
| 23 | Ratb of lenglh/maximum width of mature leaf on center part of first-year shoot | Measurement | 3<br>5<br>7 |
| 24 | Shape b cross- section of center part of mature leaf on center part of first-year shoot | Observation | 1<br>2<br>3 |
| 25 | Recurvature of leaf blade apex of mature leaf on center part of first-year shoot | Observation | 1<br>9 |
| 26 | Shape of mature leaf base on center part of first-year shoot | Observation | 1<br>2<br>3 |
| 28 | Color of mature leaf on center part of first-year shoot | Observation | 1<br>2<br>3 |
| 29 | Red mid-vein on the lower stde of mature leaf on center part of first-year shoot | Observation | 1<br>9 |
| 30 | Length of petiole of mature leaf on center part of first-year shoot | Measurement mm | 3<br>5<br>7 |
| 31 | Presence or absence of nectaries on petiole immedately after completion of extension of petiole | Observation | 1<br>9 |
| 32 | Shape of nectaries on petiole | Observation | 1<br>2 |
| 33 | Predominant number of nectaries on petiole | Measurement | 1<br>2 |
| 34 | Weight of mature fruit | Measurement g | 1<br>3<br>5<br>7<br>9 |
| 35 | Shape of mature fruit viewed from frontside (suture side) | Observation | 1<br>2<br>3<br>4<br>5 |
| 36(*) | Shape a# fruit apex of mature fruit | Observation | 1<br>2<br>3<br>4<br>5 |
| 37 | Symmetry of mature fruit, viewed from fruit apex | Observation | 1<br>2 |

TABLE 1-continued (Table of Characteristics)

| | | | |
|---|---|---|---|
| 38 | Depth of suture at eguatorial part of mature fruit | Observation | 3<br>5<br>7 |
| 39 | Depth of stalk cavity of mature fruit | Measurement cm | 3<br>5<br>7 |
| 40 | Width of stak cavity of mature fruit | Measurement cm | 3<br>5<br>7 |
| 41 | Ground color of fruit skin of mature fruit | Observation | 1<br>2<br>3<br>4<br>5<br>6<br>7<br>8<br>9<br>10 |
| 42 | Presence or absence of over color of fruit skin of mature fruit | Observation | 1<br>9 |
| 43 | Hue of over color of fruit skin of mature fruit | Observation | 1<br>2<br>3<br>4<br>5<br>6 |
| 44 | Pattern of over color of fruit skin of mature fruit | Observation | 1<br>2<br>3<br>4 |
| 45 | Extent of over color on mature fruit | Observation | 1<br>3<br>5<br>7<br>9 |
| 46 | Presence or absence of pubescence on surface of mature fruit | Observation | 1<br>9 |
| 48 | Thickness of fruit skin of mature fruit | Measurement mm | 3<br>5<br>7 |
| 49 | Adherence of fruit skin to fruit flesh | Observation | 1<br>3<br>5<br>7<br>9 |
| 50 | Firmness of fruit flesh at equatorial part of mature fruit | Measurement | 1<br>3<br>5<br>7<br>9 |
| 51 | Ground color of fruit flesh of mature fruit | Observation | 1<br>2<br>3<br>4<br>5<br>6<br>7<br>8 |
| 52 | Intensity of anthocyanin coloration at immedately under fruit skin of mature fruit | Observation | 1<br>2<br>3 |
| 53 | Intensity of anthocyanin coloration in fruit flesh of mature fruit | Observation | 1<br>2<br>3 |
| 54 | Intensity of anthocyanin coloration around stone of mature fruit | Observation | 1<br>2<br>3 |
| 55 | Texture of fruit flesh at equatorial part of mature fruit | Observation | 1<br>2 |
| 56 | Degree of sweetness of fruit flesh at equatorial part of mature fruit | Measurement | 3<br>5<br>7 |
| 57 | Degree of acidity of fruit flesh at equatorial part of mature fruit | Measurement | 3<br>5<br>7 |

TABLE 1-continued (Table of Characteristics)

| | | | |
|---|---|---|---|
| 58 | Relative weight of stone to mature fruit (weight of stone whole weight of fruit) | Measurement | 3<br>5<br>7 |
| 59 | Shape in lateral view (non- suture side) of stone of mature fruit | Observation | 1<br>2<br>3<br>4 |
| 60 | Intensity of brown cobr of stone of mature fruit | Observation | 3<br>5<br>7 |
| 61 | Relief of surface of stone of mature fruit | Observation | 1<br>2<br>3<br>4 |
| 62 | Tendency of splitting of stone of mature fruit | Measurement | 1<br>3<br>5<br>7<br>9 |
| 63 | Presence or absence of adherence of stone (or free stone) to fruit flash of mature fruit | Observation | 1<br>9 |
| 64 | Degree of adherence of stone (or free stone) to fruit flesh of mature fruit | Observation | 3<br>5<br>7 |
| 65 | Timing of first leaf bud burst | Observation | 1<br>3<br>5<br>7<br>9 |
| 66 | Timing of beginning of seguential flowering | Observation | 1<br>3<br>5<br>7<br>9 |
| 67 | Length of duration of flowering | Observation | 3<br>5<br>7 |
| 68 | Timing of maturity of fruit for consumption | Observation | 1<br>3<br>5<br>7<br>9 |
| 69 | Tendency to preharvest drop | Observation | 1<br>3<br>5<br>7<br>9 |

| | State ¶ | | |
|---|---|---|---|
| Character No. | 'Sweet Rei' (present tree) | 'Sweet venus' (comparator 1) | 'Kawanakajma Hakuto' (comparator 2) |
| 1 | very smal<br>smal<br>medium<br><br>semi-large 2.5 to 3 m (Height)<br>large<br>very large | very small<br>small<br>medium<br><br>semi-large 3.8 m (Height)<br>large<br>very large | very small<br>small<br>medium 2.7 m (Height)<br>semi-large<br><br>large<br>very large |
| 2 | weak<br>medium<br>strong | weak<br>medium<br>strong | weak<br>medium<br>strong |
| 3 | upright<br>semi-upright<br>spreadmg<br>drooping<br>weeping | upright<br>semi-upright<br>spreadng<br>drooping<br>weeping | upright<br>semi-upright<br>spreading<br>droophg<br>weeping |
| 4 | thin<br>medium<br>thick | thin<br>medium<br>thick | thin<br>medium<br>thick |
| 5 | very short<br>short<br>medium<br>long<br>long | very short<br>short<br>medium<br>bog<br>very long | very short<br>short<br>medium<br>long<br>very long |
| 6 | absent<br>present | absent<br>present | absent<br>present |
| 7 | weak<br>medium<br>strong | weak<br>medium<br>strong | weak<br>medium<br>strong |
| 8 | sparse<br>medium<br>dense | sparse<br>medium<br>dense | sparse<br>medium<br>dense |
| 9 | isolated<br>in groups<br>of two or more | isolated<br>in groups<br>of two or more | isolated<br>in groups<br>of two or more |
| 10 | showy<br>non showy | showy<br>non showy | showy<br>non showy |
| 11 | greenish yellow<br>strong yellowish green (RHS Code: N144A) | greenish yelow<br>orange (RHS Code: 33A) | greenish yelow<br>orange (RHS Code: 25A) |
| 12 | white<br>very ligft pink<br>light purplish pink (RHSCode: 65B)<br>medium pink<br>dark pink<br>violet pink<br>red | white<br>very light pink<br>ight pink (RHSCode: 62B)<br>medium pink<br>dark pink<br>violet pink<br>red | white<br>very fight pink<br>light pink (RHS Code: 62D)<br>medium pink<br>dark pink<br>violet pink<br>red |
| 13 | narrow eliptic<br>broad elliptic<br>round | nanow eliptic<br>broad eliptic<br>round | narrow eliptic<br>broad eliptic<br>round |
| 14 | very small<br>smal<br>medium 3.27 cm<br>large<br>very large | very small<br>small<br>medium 3.68 cm<br>large<br>very large | very small<br>small<br>medium 3.5 $cm^2$<br>large<br>very large |
| 15 | five<br>6 or more | five<br>6 or more | five<br>6 or more |
| 16 | below<br>same level<br>above | below<br>same level<br>above | below<br>same level<br>above |
| 17 | below<br>same level<br>above | below<br>same level<br>above | bebw<br>same level<br>above |
| 18 | absent<br>present | absent<br>present | absent<br>present |
| 19 | absent<br>present | absent<br>present | absent<br>present |
| 21 | short<br>medium<br>long 18.61 cm | short<br>medium 16.61 cm<br>long | short 13.2 cm<br>medium<br>long |
| 22 | narrow<br>medium 3.71 cm<br>broad | narrow<br>medium 3.94 cm<br>broad | narrow 3.35 cm<br>medium<br>broad |
| 23 | small<br>medium<br>large 5.02 cm | small<br>medium 4.22 cm<br>large | small 3.95 cm<br>medium<br>large |
| 24 | concave<br>flat<br>convex | concave<br>flat<br>convex | concave<br>fiat<br>convex |
| 25 | absent<br>Present | absent<br>Present | absent<br>Present |
| 26 | acute<br>approximately right angle<br>obtuse | acute<br>approximately right angle<br>obtuse | acute<br>approximately right angle<br>obtuse |
| 28 | greenish yellow<br>dark green (RHS Code: 136A)<br>purplish red | greenish yelow<br>green (RHS Code: 135B)<br>purplish red | greenish yellow<br>green (RHS Code: 134A)<br>purpish red |
| 29 | absent<br>Present | absent<br>Present | absent<br>Present |
| 30 | short<br>medium 1.34 cm<br>long | short<br>medium 1.09 cm<br>long | short 0.6 cm<br>medium<br>long |
| 31 | absent<br>present | absent<br>present | absent<br>present |
| 32 | round | round | round |

TABLE 1-continued (Table of Characteristics)

| | | | |
|---|---|---|---|
| | reniform | reniform | reniform |
| 33 | two | two | two |
| | 3 or more | 3 or more | 3 or more |
| 34 | verysmal | very small | very small |
| | smal | small | small |
| | medium 208.7 g | medium | medium |
| | large | large 247.4 g | large 235.7 g |
| | very large | very large | very large |
| 35 | broad oblate | broad oblate | broad oblate |
| | oblate | oblate | oblate |
| | round | rowd | round |
| | ovate | ovate | ovate |
| | elliptic | elliptic | eliptic |
| 36(*) | prominently pointed | prominenlly pointed | prominently pointed |
| | weakly pointed | weakly pointed | weakly pointed |
| | flat | flat | flat |
| | weakly depressed | weakly depressed | weakly depressed |
| | strongly depressed | strongly depressed | strongly depressed |
| 37 | asymmetric | asymmetric | asymmetric |
| | symmetric | symmetric | symme&lc |
| 38 | weak | weak | weak |
| | medium | medium | medium |
| | strong | strong | strong |
| 39 | shallow | shallow | shalow |
| | medium 1.3 cm | medium 1.3 cm | medium 1.5 cm |
| | deep | deep | deep |
| 40 | narrow | narrow | narrow |
| | medium | medium | medium |
| | broad | broad | broad |
| 41 | green | green | green |
| | cream green | cream green | cream green |
| | greenish white | geenish white | greenish while |
| | cream white | cream white | cream white |
| | cream | cream | cream |
| | pink white | pink white | pink white |
| | greenish yellow | geerish yelow | greenish yelbw |
| | cream yellow | cream yellow | cream yelbw |
| | yellow | yelow | yelbw |
| | orange yellow | orange yelow | orange yelbw |
| 42 | absent | absent | absent |
| | present | present | present |
| 43 | orange red | orange red | orange red |
| | pink | pink | pink |
| | pink red | pink red | pink red |
| | light red | ightred | light red |
| | medium red | medium red | medium red |
| | dark red | dark red | dark red |
| | (RHSCode: 59A) | | |
| 44 | solid flush | sold flush | sold flush |
| | striped | striped | striped |
| | mottled | mottled | mottled |
| | marbled | marbled | marbled |
| 45 | absent or very small | absent or very small | absent or very small |
| | smat | small | small |
| | medium | medium | medium |
| | large | large | large |
| | very large | very large | very large |
| 46 | absent | absent | absent |
| | present | present | present |
| 48 | thin | ftin | thin |
| | medium | medium | medium |
| | thick | thick | thick |
| 49 | absent or very weak | absent or very weak | absent or very weak |
| | weak | weak | weak |
| | medium | medium | medium |
| | strong | strong | strong |
| | very strong | very strong | very strong |
| 50 | very soft | very soft | very soft |
| | soft | soft | soft |
| | medium | medium | medium |
| | firm | firm | firm |
| | very firm | very firm | very firm |
| 51 | greenish white | greenish white | greenish white |
| | white | white | whte |
| | yellowish white | cream white | cream white |
| | (RHS Code: 155B) | | (RHS Code: 40) |

TABLE 1-continued (Table of Characteristics)

| | | | |
|---|---|---|---|
| | light yelow | light yelow | light yellow |
| | yellow | yellow | yellow |
| | | (RHS Code: 23A) | |
| | orange yellow | orange yellow | orange yellow |
| | orange | orange | orange |
| | red | red | red |
| 52 | absent or very | absent or very | absent or very |
| | weakly expressed | weakly expressed | weekly expressed |
| | (RHS Code: 588) | | |
| | weakly expressed | weakly expressed | weakly expressed |
| | strongly expressed | strongly expressed | strongly expressed |
| 53 | absent or very | absent or very | absent or very |
| | weakly expressed | weakly expressed | weekly expressed |
| | (RHS Code: N66C) | | |
| | weakly expressed | weakly expressed | weakly expressed |
| | strongly expressed | strongly expressed | strongly expressed |
| 54 | absent or very | absent or very | absent or very |
| | weakly expressed | weakly expressed | weakly expressed |
| | weakly expressed | weakly expressed | weakly expressed |
| | red purple | strongly expressed | strongly expressed |
| | (RHS Code: N57B) | | |
| 55 | not fibrous | not fibrous | not fibrous |
| | fibrous | fibrous | fibrous |
| 56 | low | bw | low |
| | medium | medium | medium |
| | high | high | high |
| 57 | low | low | bw |
| | medium | medium | medium |
| | high | high | high |
| 58 | small | small | small |
| | medium | medium | medium |
| | large | large | large |
| 59 | oblate | oblate | oblate |
| | round | round | round |
| | elliptic | elliptic | eliptic |
| | obovate | obovate | obovate |
| 60 | light | light | light |
| | medium | medium | medium |
| | | (RHS Code: N170B) | |
| | dark | dark | dark |
| | (RHS Code: 185B) | | |
| 61 | small pits | small pits | small pits |
| | large pits | large pits | large pts |
| | grooves | grooves | grooves |
| | pits and grooves | pits and grooves | pits and grooves |
| 62 | absent or very low | absent or very low | absent or very low |
| | low | low | low |
| | medium | medium | medium |
| | high | high | high |
| | very high | very high | very high |
| 63 | absent | absent | absent |
| | Present | Present | Present |
| 64 | weak | weak | weak |
| | medium | medium | medium |
| | strong | strong | strong |
| 65 | very early | very early | very early |
| | early | early | early |
| | medium around March 25 | medium March 19 | medium March 19 |
| | late | late | late |
| | very late | very late | very late |
| 66 | very early | very early | very early |
| | early | early | early |
| | medium | medium | medium |
| | late | late | late |
| | very late | very late | very late |
| 67 | short | short | short |
| | medium 10 days | medium 10 days | medium 10 days |
| | long | long | long |
| 68 | very early | very early | very early |
| | early | early | early |
| | medium | medium | medium |
| | late August 25 to September 5 | late August 28 to September 7 | late August 20 to August 30 |
| | very late | very late | very late |

TABLE 1-continued

| (Table of Characteristics) | | | |
|---|---|---|---|
| 69 | absent or very weak<br>weak<br>medium<br>strong<br>very strong | absent or very weak<br>weak<br>medium<br>strong<br>very strong | absent or very weak<br>weak<br>medium<br>strong<br>very strong |

¶ The boxed words (such as "medium", "absent" and "very late") under each cultivar name indicate the properties of the respective cultivars

What is claimed is:

1. A new and distinct variety of white nectarine tree (*Prunus persica* (L.) Batsch var. *nucipersica* (Suckow) C.K. Schneid.) denominated 'SWEET REI', as illustrated and described herein.

* * * * *

The variety for application for registration: C-21 (SWEET REI) (bagged)
Photographed date: August 31, 2017

The variety for application for registration: C-21 (SWEET REI) (bagged)
Photographed date: August 31, 2017

The variety for application for registration: C-21 (SWEET REI) (bagged)
Photographed date: August 31, 2017

The variety for application for registration:
C-21 (SWEET REI) (bagged)
Photographed date:
September 1, 2017

(Non-bagged)

The variety for application for registration:
C-21 (SWEET REI) (bagged)
Photographed date:
September 1, 2017

SWEET VENUS

Kawanakajimahakuto

The variety for application for registration: C-21 (SWEET REI) (bagged)
Photographed date: August 31, 2017

The variety for application for registration:
C-21 (SWEET REI) (bagged)
Photographed date:
September 1, 2017

SWEET VENUS

Kawanakajimahakuto

The variety for application for registration: C-21 (SWEET REI)
Photographed date: April 10, 2018

The variety for application for registration: C-21 (SWEET REI)
Photographed date: April 10, 2018

The variety for application: C-21 (SWEET REI)
Photographed date: April 10, 2018

SWEET VENUS

Kawanakajimahakuto

The variety: C-21 (SWEET REI)

SWEET VENUS

Kawanakajimahakuto

The variety for application for registration: C-21 (SWEET REI) (bagged)
Photographed date: September 1, 2017

SWEET VENUS

Kawanakajimahakuto

The variety for application for registration: C-21 (SWEET REI)
Photographed date: September 1, 2017

The variety for application for registration:
C-21 (SWEET REI) (bagged)
Photographed date:
September 1, 2017

SWEET VENUS

Kawanakajimahakuto